United States Patent [19]

Keith et al.

[11] Patent Number: 4,492,685

[45] Date of Patent: Jan. 8, 1985

[54] PROTECTIVE SKIN MATRIX

[75] Inventors: Alec D. Keith, Miami, Fla.; Wallace Snipes, State College, Pa.

[73] Assignee: Key Pharmaceuticals, Inc., Miami, Fla.

[21] Appl. No.: 574,844

[22] Filed: Jan. 30, 1984

Related U.S. Application Data

[63] Continuation of Ser. No. 425,853, Sep. 28, 1982, abandoned, which is a continuation of Ser. No. 295,689, Aug. 24, 1981, abandoned, which is a continuation of Ser. No. 163,105, Jun. 26, 1980, abandoned, which is a continuation of Ser. No. 109,242, Jan. 3, 1980, abandoned, which is a continuation-in-part of Ser. No. 2,565, Jan. 11, 1979, abandoned, and Ser. No. 47,084, Jun. 11, 1979, abandoned.

[30] Foreign Application Priority Data

Aug. 14, 1979 [JP] Japan ................. 54-103459

[51] Int. Cl.³ ................. A61K 9/70; A61L 15/03; A61F 13/00
[52] U.S. Cl. ................. 424/28; 424/78; 424/80
[58] Field of Search ................. 424/28, 78, 80

[56] References Cited

U.S. PATENT DOCUMENTS

| | | | |
|---|---|---|---|
| 2,127,896 | 10/1938 | Vohrer | 18/55 |
| 2,138,751 | 11/1938 | Vohrer | 18/54 |
| 2,155,658 | 4/1939 | Herrmann et al. | 424/78 |
| 2,160,503 | 5/1939 | Herrmann | 424/78 |
| 2,340,866 | 2/1944 | Dangelmajor | 260/8 |
| 2,491,642 | 12/1947 | Brant | 264/213 |
| 2,693,438 | 11/1954 | Ward | 424/28 |
| 3,214,338 | 10/1965 | Ehrlich | 424/28 |
| 3,249,109 | 5/1965 | Maeth | 128/268 |
| 3,287,222 | 11/1966 | Larde et al. | 424/28 |
| 3,577,516 | 5/1971 | Gould et al. | 424/81 |
| 3,598,123 | 8/1971 | Zaffaroni | 128/268 |
| 3,608,070 | 9/1971 | Nouvel | 424/80 |
| 3,627,871 | 12/1971 | Groves et al. | 424/78 |
| 3,731,683 | 5/1973 | Zaffaroni | 128/156 |
| 3,803,300 | 4/1974 | Pospischil | 424/28 |
| 3,892,905 | 7/1975 | Albert | 252/90 |
| 4,076,798 | 2/1978 | Casey et al. | 424/22 |
| 4,210,633 | 7/1980 | Takruri et al. | 424/28 |

FOREIGN PATENT DOCUMENTS

| | | |
|---|---|---|
| 2239355 | 2/1974 | Fed. Rep. of Germany . |
| 1505318 | 12/1967 | France . |
| 2245161 | 4/1975 | France . |
| 2437830 | 4/1980 | France . |
| 48-92522 | 11/1973 | Japan . |
| 49-30525 | 3/1974 | Japan . |
| 49-45952 | 5/1974 | Japan . |
| 49-48728 | 12/1974 | Japan . |
| 50-112511 | 3/1975 | Japan . |
| 50-56385 | 5/1975 | Japan . |
| 52-38016 | 3/1977 | Japan . |
| 53-50320 | 5/1978 | Japan . |
| 933668 | 8/1963 | United Kingdom ............ 424/78 |
| 1108837 | 4/1968 | United Kingdom . |
| 1465665 | 2/1977 | United Kingdom . |
| 2021610 | 12/1979 | United Kingdom ............ 424/80 |
| 2021950 | 12/1979 | United Kingdom . |
| 219116 | 3/1973 | U.S.S.R. . |

OTHER PUBLICATIONS

Peierls Modern Plastics 18:53–56, Feb. 1941, Polyvinyl Alcohol Plastics.
Hess et al., Rubber Age 53:431–433, Aug. 1943, Molding Polyvinyl Alcohol.
Ita et al. Bulletin Pharm. Research Inst., Osaka Medical College (2) 1–3 (1951) II. "On a New Water-Soluble Ointment".
Hirai Bull. Inst. Chem. Koyoto Univ. 33:21–37 (1955) The Gel-Elasticity of High Polymers.
Langhammer et al., Naturwissenschaften 43:125–126 (1956) (PVP-PVA) (PVP-PVA) Nehring Plaste und Kautschuk 3:279–280 (1956).
Ward et al. Amer. Perf. & Cosmetics 79: 53–55 Nov. 1964, The Use of Polyvinyl Alcohol in Film-Forming Bases.
Ward et al., J. Soc. Cos. Chem. 15:327–335 (1964) Cosmetic Applications of Polyvinyl Alcohol.
Toyoshima, K. "Compatibility of Polyvinyl Alcohol with Other Water-Soluble High Polymers" in Finch et al Ed. (1967?) Polyvinyl Alcohol:Properties & Applications.
Ban et al., Pharmazie 29 H9: 597–602, (1974), (PVP-PVA).
Nagy et al. "Formation of Disperse Structures in Polymer Gels" Proc. Int. Conf. Colloid & Surface Science, Budapest, Hungary, Sep. 1775, Wolfram et al. p. 447.
CA.83.152389k(1975), 81.137166A(1974), 80.137177f(1974), 79.498456(1973) 97:49594A(1972) CA.75.154276(1971).
CA.92,193166h(1950) 91.112398w(1979) 89.30689m(1975) 85.141144N(1976) 84.199686K(1976) CA.82.21827h175204w(1975) 81.41348K(1974) 81.163498W(1914).

*Primary Examiner*—Shep K. Rose
*Attorney, Agent, or Firm*—Wegner & Bretschneider

[57] ABSTRACT

A protective skin matrix is provided which is particularly suited for the protection of burned or wounded patients. The matrix may be either cured, applied in sheets, or painted or sprayed directly onto the burned or wounded patient. The protective skin matrix includes polyvinylpyrrolidone, polyvinylalcohol, and glycerol.

9 Claims, No Drawings

PROTECTIVE SKIN MATRIX

CROSS-REFERENCE TO RELATED CASES

This application is a continuation of Ser. No. 425,853, filed Sept. 28, 1982, which is a continuation of Ser. No. 295,689, filed Aug. 24, 1981, which in turn is a continuation of Ser. No. 163,105, filed June 26, 1980, which is a continuation-in-part of U.S. application Ser. No. 109,242, filed Jan. 3, 1980, which in turn is a continuation-in-part of U.S. application Ser. No. 2,565, filed Jan. 11, 1979, and Ser. No. 47,084, filed June 11, 1979, all now abandoned.

SUMMARY OF THE INVENTION

A protective skin matrix is provided which is particularly suited for the protection of burned or wounded patients. In a first aspect of the present invention, the matrix is cast and cured, and thereafter cut into pieces or sheets of an appropriate size for use wth the burned or wounded subject. In a second aspect of the invention, a polymeric composition forming the matrix is applied directly in the uncured state onto the burned or wounded patient, for example, by painting the composition onto the area requiring protection or by use of a spray technique. The "cure" takes place in situ on the burned or wounded area.

DETAILED DESCRIPTION OF THE INVENTION

In accordance with the first aspect of the present invention, the polymeric matrix comprises polyvinylpyrrolidone, polyvinylalcohol, glycerol, and water.

Polyvinylpyrrolidone is present in an amount of from about 2 to about 10%, preferably from about 3 to about 8% by weight. The polyvinylpyrrolidone, has a molecular weight of from about 25,000 to about 100,000, preferably from about 35,000 to about 50,000. The polyvinylalcohol is present in an amount of from about 2 to about 15%, preferably from about 6 to about 12%, by weight. The polyvinylalcohol has a molecular weight of from about 50,000 to about 150,000, preferably at least about 100,000. A preferred range is from about 120,000 to about 135,000. The glycerol is present in an amount of from about 2 to about 20%, preferably from about 2 to about 18% by weight. Preferably, the glycerol is a 96% aqueous glycerol solution. (The percentages given above are for the uncured state.)

As a preferred embodiment, there is provided a polymeric diffusion matrix which comprises in its uncured state and on a weight basis: about 10.5% polyvinylalcohol (molecular weight 126,000); about 6% polyvinylpyrrolidone (molecular weight 40,000); about 15% glycerol; and the balance water.

The relative weight amounts of polyvinylalcohol to polyvinylpyrrolidone that have been considered range from about 3:1 to about 1:1. In actual practice, however, at a range of about 3:1, less than optimum results are obtained with the burn matrix swelling to an unacceptable degree, and at the ratio of 1:1 the burn matrix tends toward being soft and sticky. Accordingly, in accordance with a preferred aspect of the present invention, it has been discovered that a weight range of polyvinylalcohol to polyvinylpyrrolidone should be between about 2:1 and about 3:2. The weight ratio of glycerol to total polymers for the burn matrix is usually less than 1, preferably about 0.5–1:1.

The amount of water which is to be utilized in the preparation of a burn matrix in accordance with the present invention in its generic aspect is related to the amount of glycerol which is used to make the burn matrix of the present invention. The amount of water by volume exceeds the amount of glycerol that is used in the initial mixture of ingredients. According to a preferred embodiment of the present invention, water is present in an amount of from about three to about seven times the amount of glycerol present in the initial mixture of ingredients. After the manufacture of the burn matrix of the present invention, the matrix is "cured" to eliminate most of the water, where water has been used in excess. The amount of time for the cure depends upon conditions such as the amount of excess water. In a preferred embodiment where 20 ml of glycerol is mixed with 100 ml water, the cure time is about ½ to 24 hours, yielding a burn matrix with an approximately equal amount of water and glycerol.

In order to prepare the burn matrix of the present invention, the water and glycerol are mixed together, preferably at a somewhat elevated temperature, e.g., 50° C. The polyvinylalcohol and the polyvinylpyrrolidone are added under agitation with the temperature being raised and with continued agitation until solution is effected. The temperature in one embodiment is raised to about 95° C. with solution being effected at that temperature. The resultant homogenous mixture is then poured onto forms which are typically of plastic or stainless steel serving as templates to produce a burn matrix having a thickness of about 0.2 to about 4 mm. Where excess water has been included in the burn matrix, the burn matrix is cured to eliminate the excess water. For example, where a 5:1 volume ratio of water to glycerol is used, the freshly prepared burn matrix is permitted to set for about 24 hours, resulting in a burn matrix having a thickness of about 0.1 to 2 mm. The preferred thickness for a "cured" burn matrix is from about 0.1 to about 2 mm.

The burn matrix polymeric composition is preferably cast to form a sheet of the matrix. After curing, the sheet is cut into smaller sheets having a suitable surface area. The smaller sheets can then be deposited on an appropriate backing layer. Alternatively, the burn matrix polymeric composition can be poured onto a backing layer to form a sheet of the matrix in intimate contact with the backing layer. The backing layer can be made of laminates comprising a polyester outer layer, a metal foil intermediate layer, and a ionomer inner layer. The matrix/backing layer laminate can be wound to form a roll of the matrix or cut into smaller sheets of suitable size.

Where drugs are to be included in the burn matrix, those drugs may be added, in the case of drugs soluble in the burn matrix, to the homogenous mixture prior to casting, or after curing of the matrix, by the physician or pharmacist at his direction shortly before the need for application arises, permitting a wider flexibility in topically applying a medicine to the patient. Generally, water-insoluble drugs may be included in the burn matrix either through original incorporation into the mixture of water and glycerol or through subsequent application of the drung into the already prepared burn matrix. Where the drug is to be applied to a typical burn matrix of the invention having a thickness of about 2 mm, the drug may be painted onto a surface of the burn matrix or the drug may be applied through other means, such as an aerosol. A sufficient period of time, e.g., 4 hours, should be provided for the drug to diffuse through the burn matrix of the present invention. In order to provide an anesthetic effect, a water-soluble anesthetic such as xylocaine may be applied through any of the above modes available for water-soluble drugs. The amount of the water-soluble drug that is to be dispersed in the burn matrix of the present invention should be in excess of the amount which is to be administered to the patient. An excess of 2 to 10 times the actual amount of drug which is to be administered to the patient should generally be used.

A water-soluble antibiotic to counter the possibility of infection should also be considered for inclusion in the burn matrix of the present invention. Because of the option of includng the specifically desired antibiotic after the preparation of the burn matrix of the present invention, the individual physician is given great latitude in selecting the desired antiobiotic to take into account the particular needs of the specific patient being treated. As an example of a water-soluble antibiotic which may be incorporated into the burn matrix of the present invention may be mentioned Penicillin VK.

Water-insoluble materials may also be desirably included in the burn matrix of the present invention. Such materials are preferably introduced directly into the initial mixture of water and glycerol at the outset of the manufacturing process for making the burn matrix of the present invention. In accordance with one aspect of the invention, there is provided a zinc substance in an amount from about 0.4 to about 2% by weight based upon the final weight of the cured burn matrix of the present invention. Zinc chelates may be used as the zinc substance of this aspect of the present invention. In accordance with a further embodiment within the scope of the present invention about 0.4 to about 2% by weight zinc or silver sulfadiazine is incorporated into the burn matrix of the present invention for retarding Pseudomonas infections or other bacterial infections.

In making zinc or silver (or other water-insoluble materials) burn matrix of the present invention, the zinc or silver material is preferably added with a small amount of the glycerol. The amount of glycerol needed to make the suspension is subtracted from the amount of glycerol initially mixed with the water. A uniform suspension of the zinc or silver compound and glycerol is added together with the water and remainder of the glycerol, preferably as the last stage prior to casting.

In addition to local anesthetics and antibiotics which can be applied to or incorporated into the burn matrix of the present invention, other topical medicines may also be applied to or incorporated in the burn matrix. Examples of useful topical drugs include fungicides, bactericides, anti-micoplasma (*E. coliplasma*), analgesics, and local anesthetics.

The amount of drug which can be incorporated into the burn matrix is up to about 10% by weight of the burn matrix. By incorporated, it is meant that the drug is added to the polymer mixture before casting. As to drugs which can be painted onto the surface of the matrix, the amount used varies in accordance with the drug applied.

If desired, a hydrophobic casting may be desired in the burn matrix of the present invention. Silicone oil may be added in amounts of about 0.1 to 10% by weight, based on the matrix, in the initial mixture of glycerol and water. Mineral oil or vegetable oil may substitute in part or whole for the silicone oil, which lowers the transdermal loss of water in the patient.

The burn matrix in accordance with the present invention is a flexible and transparent polymer which is suited for being applied directly to a burned portion of the patient being treated for most parts of the body. After hydration, the burn matrix is highly flexible and will adhere mildly to the skin. The degree of adherence is sufficient to hold the burn matrix in place but not enough to injure the patient's skin when it is removed. It is contemplated that the burn matrix should be replaced periodically, typically at 24-hour (or longer) intervals.

The burn matrix of the present invention may be stored for prolonged periods, particularly when placed in a sealed container.

Guar gum (mw 220,000; Merck Index 4425, 9th ed.) is optionally incorporated into the polymer mixture in an amount of up to about 3%, preferably about 2% by weight, based upon the cured composition weight. The composition of the present invention with the added guar gum is provided for enhanced adhesive properties to the skin.

In a second aspect of the present invention, the uncured polymeric mixture, which becomes the matrix after curing, is applied directly to the patient. Then, curing takes place in situ on the skin of the patient. This aspect of the invention has particularly advantage with large or irregular shaped wounds, and particularly with complex surface topography, e.g., ears.

A cure acclerator is advantageously applied to the coated area of the skin, typically by spraying on a dilute solution of up to about 10% and preferably up to about 7% of the active cure accelerator. In a preferred embodiment a 5% sodium borate solution is sprayed onto the already-coated skin as a cure accelerator. Other cure accelerators are sodium phosphate and sodium carbonate.

Drugs with hydrocarbon-solubility may be incorporated into the burn or wound matrix of the present invention, but are generally accompanied by mild detergents or dispersing agents to facilitate uniform distribution in the matrix structure. As an example of a drug may be mentioned corticosteroids and as a dispersing agent may be mentioned Tween 20 or phosphatides.

The invention is illustrated by the following non-limiting Examples:

EXAMPLE I

There are mixed 100 ml water and 20 ml glycerol and the mixture is heated to about 50° C. Then 8 gm of polyvinylalcohol (molecular weight 126,000, 100% hydrolyzed) are slowly added while the preparation is undergoing rapid agitation. After the polyvinylalcohol is uniformly dispersed, 5 gm polyvinylpyrrolidone (molecular weight 40,000) is added with continued stirring. The preparation is then heated to about 95° C. until solution is effected.

EXAMPLE II

The product of Example I is poured onto a stainless steel plate resulting in an uncured matrix having a thickness of about 3 to 4 mm. The burn matrix is cured by letting water evaporate for about 24 hours, leaving a cured burn matrix having a thickness of about 1 to about 2 mm.

The burn matrix has the following compositions:

| Ingredients | uncured | % by weight cured |
| --- | --- | --- |
| glycerol | 17.9 | 34.6 |
| polyvinylalcohol | 5.8 | 11.3 |
| polyvinylpyrrolidone | 3.6 | 7.0 |
| water | 72.7 | 47.0 |

EXAMPLE III

A piece of the cured burn matrix of Example II is placed on a test system of 10% aqueous gelatin cast into a petri plate, to serve as a model for testing the burn matrix. On this model, it was found that the burn matrix of the present invention does not appreciably swell but does permit a small amount of water evaporation and further permits the exchange of some gases by diffusion processes across the perpendicular dimension of the burn matrix. The burn matrix of the present invention retards the loss of water vapor from a 10% gelatin preparation by approximately a factor of 10.

EXAMPLE IV

A one-inch square piece of the cured burn matrix of Example II is used as a model for preparing a burn matrix with water-soluble medicinal additives. Painted onto one side of the burn matrix of Example II is 10 mg of Xylocaine. After painting the Xylocaine onto the burn matrix, the burn matrix is permitted to stand for about 4 hours, resulting in a burn matrix having Xylocaine diffused therein.

EXAMPLE V

In place of the Xylocaine of Example IV, 30 mg of Penicillin VK is applied to the burn matrix, resulting in a burn matrix having antibiotic properties over the 24 hour period desired for the life of the burn matrix.

EXAMPLE VI

Example IV is repeated, except that in addition to the Xylocaine, there is also simultaneously painted onto the burn matrix 30 mg of Penicillin VK. The resultant burn matrix provides both antibiotic protection against infection and relief from pain over an extended period, due to the slow release of the Xylocaine over a prolonged period.

EXAMPLE VII

The procedure of Example I is repeated, with the following variations: 18 ml instead of 20 ml glycerol is used. In addition, sufficient zinc sulfadiazine to make up 1% by weight of the final cured burn matrix is suspended in 2 ml glycerol. This suspension is added to the mixture of other ingredients as the last step prior to pouring onto the stainless steel plate.

The resultant cured burn matrix provides the additional advantage of protecting the burn victim over an extended period against Pseudomonas infection. In place of zinc sulfadiazine, silver sulfadiazine may be used.

EXAMPLE VIII

The procedure of Example VII is repeated except that the zinc sulfadiazine is replaced by 20 mg of Cephalosporin, resulting in a burn matrix having antibiotic properties.

EXAMPLE IX

The procedure of Example I is repeated except that 2% by weight guar gum is added to the polyvinylpyrrolidone, the percentage being by weight based upon uncured composition weight. A composition suitable for casting as in Example II is provided.

EXAMPLE X

The product of Example II is painted onto the skin of a patient and cured. The burn matrix formed in situ creates a protective barrier and has properties comparable to the burn matrix applied in the already cured form. Curing takes place in a period of from about 3 to 30 minutes, depending on the thickness of the coating.

EXAMPLE XI

The procedure of Example X is repeated, except that after the composition has been painted onto the skin of the patient, sodium borate was sprayed over the coated skin. Curing was greatly accelerated to a time under one minute.

What is claimed is:

1. A cured self-supporting polymeric diffusion matrix suitable for providing protection to a burned or wounded patient, said matrix being formed by:
    (a) heating an aqueous system comprising 2 to 20% glycerol, 4 to 30% polyvinyl alcohol molecular weight 50,000 to 150,000, 2 to 20% polyvinylpyrrolidone molecular weight 25,000 to 100,000, and the balance water, the weight ratio of polyvinyl alcohol to polyvinylpyrrolidone being 2:1 to 3:2, the weight ratio of glycerol to polyvinyl alcohol and polyvinylpyrrolidone together being 0.5:1 to 1:1, and weight ratio of water to glycerol being 3:1 to 7:1, until solution occurs,
    (b) casting or molding the resultant solution, and
    (c) curing the cast or molded solution by permitting it to stand for one-half to twenty-four hours.

2. A method of protecting a burned or wounded area of a patient over a prolonged period of time, which comprises placing over said burned or wounded area of said patient a cured polymeric diffusion matrix, said matrix being formed by:
    (a) heating an aqueous system comprising 2 to 20% glycerol, 4 to 30% polyvinyl alcohol molecular weight 50,000 to 150,000, 2 to 20% polyvinylpyrrolidone molecular weight 25,000 to 100,000, and the balance water, the weight ratio of polyvinyl alcohol to polyvinylpyrrolidone being 2:1 to 3:2, the weight ratio of glycerol to polyvinyl alcohol and polyvinylpyrrolidone together being 0.5:1 to 1:1, and weight ratio of water to glycerol being 3:1 to 7:1, until solution occurs,
    (b) casting or molding the resultant solution, and
    (c) curing the cast or molded solution by permitting it to stand for one-half to twenty-four hours.

3. The polymeric diffusion matrix of claim 1 further comprising a drug and wherein said drug is an antibiotic, an antiseptic, a local anesthetic, an analgesic, a fungicide, a bactericide, or an anti-micoplasma.

4. The method of claim 2 wherein said matrix also contains a drug and said drug is an antibiotic, an antiseptic, a local anesthetic, an analgesic, a fungicide, a bactericide, or an anti-micoplasma.

5. The method of claim 4 wherein said drug is an antiseptic.

6. The method of claim 5 wherein said drug is an antibiotic.

7. The method of claim 6 wherein said drug comprises a mixture of an antiseptic and an antibiotic.

8. The polymeric diffusion matrix of claim 3 wherein said drug is an antiseptic.

9. The polymeric diffusion matrix of claim 3 wherein said drug is an antibiotic.

* * * * *